(12) United States Patent
Jandaghi et al.

(10) Patent No.: US 10,420,757 B2
(45) Date of Patent: Sep. 24, 2019

(54) PANCREATIC CANCER THERAPY AND DIAGNOSIS

(71) Applicants: Deutsches Krebsforschungszentrum Stiftung des Öffentlichenrechts, Heidelberg (DE); The Royal Institution for the Advancement of Learning/McGill University, Montreal (CA)

(72) Inventors: Pouria Jandaghi, Dossenheim (DE); Jörg Hoheisel, Wiesbaden (DE); Yasser Riazalhosseini, Montreal (CA)

(73) Assignees: Deutsches Krebsforschungszentrum Stiftung des Öffentlichenrechts, Heidelberg (DE); The Royal Institution for the Advancement of Learning/McGill University, Montreal (CA)

( * ) Notice: Subject to any disclaimer, the term of this patent is extended or adjusted under 35 U.S.C. 154(b) by 184 days.

(21) Appl. No.: 15/304,598

(22) PCT Filed: Apr. 17, 2015

(86) PCT No.: PCT/EP2015/058380
§ 371 (c)(1),
(2) Date: Oct. 17, 2016

(87) PCT Pub. No.: WO2015/158890
PCT Pub. Date: Oct. 22, 2015

(65) Prior Publication Data
US 2017/0035746 A1     Feb. 9, 2017

(30) Foreign Application Priority Data

Apr. 17, 2014   (EP) .................................... 14165053

(51) Int. Cl.
| | | |
|---|---|---|
| A61K 45/06 | (2006.01) | |
| A61K 31/454 | (2006.01) | |
| A61K 31/7068 | (2006.01) | |

(52) U.S. Cl.
CPC ........ *A61K 31/454* (2013.01); *A61K 31/7068* (2013.01); *A61K 45/06* (2013.01)

(58) Field of Classification Search
CPC .. A61K 45/06; A61K 31/454; A61K 31/7084; A61K 2300/00
See application file for complete search history.

(56) References Cited

U.S. PATENT DOCUMENTS 8,445,517 B2 * 5/2013 Frank ................... A61K 31/085
                                                            514/256
9,283,192 B2 * 3/2016 Mullen ................ A61K 9/2013
2011/0144043 A1   6/2011 Frank ............................ 514/26

FOREIGN PATENT DOCUMENTS

| WO | WO 2004/103262 | 12/2004 |
| WO | WO 2009/049242 | 4/2009 |
| WO | WO 2009/070331 | 6/2009 |
| WO | WO 2012/116432 | 9/2012 |

OTHER PUBLICATIONS

Coufal et al., "Increased local dopamine secretion has growth-promoting effects in cholangiocarcinoma," *International Journal of Cancer*, 2010; 126(9): 2112-2122.
Kim et al., "Haloperidol induces demethylation and expression of the *dual specificity phosphatase 6* gene in MIA PaCa-2 human pancreatic cancer cells," *Life Science*, 2012; 91: 1317-1322.
Moore et al., "Erlotinib Plus Gemcitabine Compared with Gemcitabine Alone in Patients with Advanced Pancreatic Cancer: A Phase III Trial of the National Cancer Institute of Canada Clinical Trials Group," *Journal of Clinical Oncology*, 2007; 25(15): 1960-1966.
International Search Report issued in Application No. PCT/EP2015/058380, dated Dec. 16, 2015.

* cited by examiner

*Primary Examiner* — Lawrence E Crane
(74) *Attorney, Agent, or Firm* — Norton Rose Fulbright US LLP

(57) ABSTRACT

The current disclosure relates to methods for treating pancreatic cancer or chronic pancreatitis in a subject comprising administering an antagonist of a dopamine receptor to the subject wherein the dopamine receptor is, in some specific cases dopamine receptor D2 (DRD2). The antagonist in some specific cases is an RNAi construct, an antibody, or a small molecule and in more specific cases pimozide or L-741,626. The disclosure also relates to diagnostic methods comprising the detection of the expression of DRD2 in pancreatic tissue and kits for doing the same.

13 Claims, 7 Drawing Sheets

Normal

CP

PDAC

A

B

A

B

PANCREATIC CANCER THERAPY AND DIAGNOSIS

CROSS-REFERENCE TO RELATED APPLICATIONS

Figure 1:
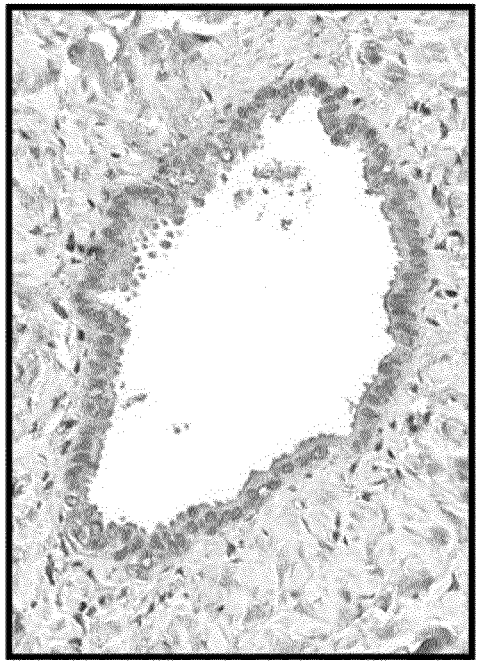
Figure 1:
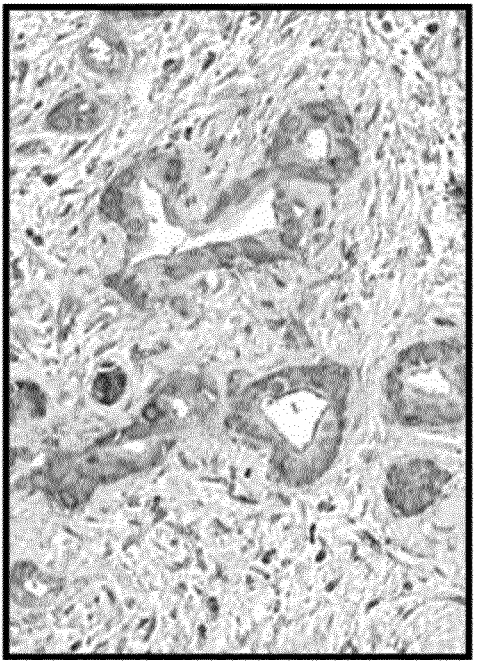
Figure 1:
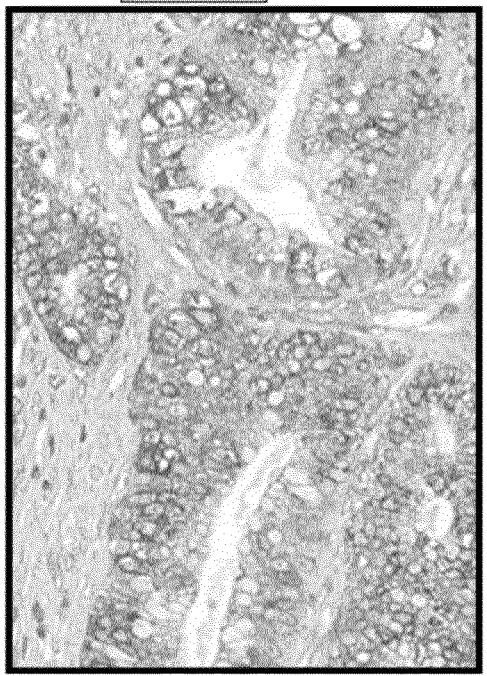

This application is a national phase application under 35 U.S.C. § 371 of International Application No. PCT/EP2015/058380 filed 17 Apr. 2015, which claims priority to European Patent Application No. 14165053.1 filed 17 Apr. 2014. The entire contents of each of the above-referenced disclosures is specifically incorporated by reference herein without disclaimer.

FIELD OF THE INVENTION

The present invention provides novel cancer therapeutics for treating pancreatic cancer, and novel diagnostic methods for detecting chronic pancreatitis and pancreatic cancer. The invention pertains to antagonists of dopamine receptors that inhibit the growth of pancreatic cancer cells. The invention in particular offers new therapy options based on the inhibition of the activity or expression of dopamine receptor D2 (DRD2). Diagnostic methods of the invention comprise the detection of the expression of DRD2 in pancreatic tissue. Diagnostic kits are also comprised.

DESCRIPTION

Pancreatic cancer has one of the highest mortality rates among all cancers and is the fourth most common cause of adult cancer death in the United States with an estimated 42,470 cases per year. About 3% of all newly diagnosed cancers are pancreatic cancers in the United States every year, with a 5 year survival rate of only 5%. The high mortality rate from pancreatic cancer is a result of the high incidence of metastatic disease at the time of diagnosis. As a result, only 5%-15% of patients are candidates for surgical resection in case of early stage diagnosis.

Pancreatic cancers can arise from both the exocrine and endocrine portions of the pancreas. Of pancreatic tumors, 95% develop from the exocrine portion of the pancreas, including the ductal epithelium, acinar cells, connective tissue, and lymphatic tissue. Approximately 75% of all pancreatic carcinomas occur within the head or neck of the pancreas, 15-20% occur in the body of the pancreas, and 5-10% occur in the tail.

Cancer recurrence can be local (in or near the same place it started) or distant (spread to organs such as the liver, lungs, or bone). When pancreatic exocrine cancer recurs, it is essentially treated the same way as metastatic cancer, and is likely to include chemotherapy if the patient can tolerate it. Typically, pancreatic cancer first metastasizes to regional lymph nodes, then to the liver, and, less commonly, to the lungs. It can also directly invade surrounding visceral organs such as the duodenum, stomach, and colon or metastasize to any surface in the abdominal cavity via peritoneal spread. Ascites may result, and this has an ominous prognosis. Pancreatic cancer may spread to the skin as painful nodular metastases. Pancreatic cancer uncommonly metastasizes to bone.

Five to ten percent of pancreatic cancer in patients is related to hereditary factors. Although the exact genetic ablation responsible for this condition has not been reported, an increased number of PDAC cases show association with inherited cancer syndromes. Another known cause of elevated pancreatic cancer risk is tobacco smoking that ranged between 3 and 1.5 times in current non-smokers and smokers respectively. Diabetes mellitus and chronic pancreatitis seem to have significant impact on the development of PDAC when compared with healthy populations.

Treatment of pancreatic cancer depends on the stage of the cancer. When the disease is confined to the pancreas and clearly separated from surrounding blood vessels (i.e. local and resectable), the treatment of choice is surgery with post-operative chemotherapy and/or radiation. When the disease encases or compresses surrounding blood vessels or has extended into adjacent structure, chemotherapy and/or radiation is proposed. In rare cases, when the patient responds well to treatment, the tumour may subsequently be surgically resected. When the disease is metastatic, chemotherapy is proposed. In most cases, these treatments do not represent a cure and the median survival ranges from 3 to 18 months depending on the stage of the disease. Each of these standard treatments is described in more detail below.

Surgical resection offers the only chance for a cure for pancreatic cancer. Approximately 20% of patients present with pancreatic cancer amenable to local surgical resection, with operative mortality rates of approximately 1 to 16%. Following surgery, median survival time is 14 months. For pancreatic cancer, the benefit of radiotherapy alone is unclear and radiotherapy is mostly used in conjunction with chemotherapy (referred to as chemoradiation). Chemotherapy may be used in patients with advanced unresectable cancer (locally advanced or metastatic) and in patients with localized disease after surgery or, sometime, beforehand in order to shrink the tumour. Gemcitabine, and to a lesser extent 5-fluorouracil (5-FU), are the chemotherapy drugs of choice to treat pancreatic cancer. Meta-analyses show that chemotherapy has significant survival benefits over best supportive care. Standard gemcitabine therapy for patients with locally advanced, unresectable, or metastatic pancreatic adenocarcinoma, provides a median overall survival (OS) of 6 months and 1-year survival rate of 21%.

Pancreatic cancer is one of the most aggressive types of common tumor and possesses multiple genetic abnormalities. This aggressive behavior of pancreatic cancer gives it the ability to obtain resistance to conventional treatment approaches such as radiation, surgery, chemotherapy or combination of them. Targeted treatments have shown successful treatment response to therapy in other solid tumors by examination of different specific small molecules which are known to be selective inhibitor against their target. This evidence supports the need for further investigation to find complementary therapy based on gene mutations or important pathways involved in the development of pancreatic cancer.

Dopamine receptors are G protein-coupled receptors that are prominent in the vertebrate central nervous system (CNS). The neurotransmitter dopamine is the primary endogenous ligand for dopamine receptors. Dopamine receptors are implicated in many neurological processes, including motivation, pleasure, cognition, memory, learning, and fine motor control, as well as modulation of neuroendocrine signalling. Abnormal dopamine receptor signalling and dopaminergic nerve function is implicated in several neuropsychiatric disorders. Thus, antipsychotics are often dopamine receptor antagonists while psychostimulants are typically indirect agonists of dopamine receptors.

Pharmacological and molecular biological studies have shown that the dopamine receptor family can be divided into five subclasses D1-5. The best characterized of these are D1 and D2. The dopamine receptor D2 (DRD2) subtype exists in a long and short form, the long form having a larger intracellular loop than the short form. These receptor subtypes appear to be anatomically, biochemically and behaviourally distinct. D1 and D2 receptors are reported to have opposite biochemical effects on adenylate cyclase activity, and stimulation of D1 and D2 receptors produces different behavioural responses. The dopamine receptor subtypes can be separately and independently modulated through the administration of selective agonists and antagonists.

Pimozide for example is a DRD2 antagonist having the chemical structure of formula I

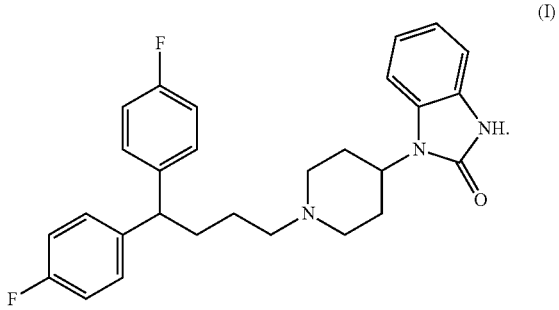 [SMILES: O=c1[nH]c2ccccc2n1C1CCN(CCCC(c2ccc(F)cc2)c2ccc(F)cc2)CC1]

Pimozide is an FDA approved drug and used in its oral preparation in schizophrenia and chronic psychosis, Tourette syndrome and resistant tics. Pimozide has been used in the treatment of delusional disorder and paranoid personality disorder. It has also been used for delusions of parasitosis. Also many other dopamine receptor antagonists and agonists are known in the art.

Document WO 2012/116432 observes the use of modulators of dopamine receptor function or expression in the treatment of leukemia. WO 2012/116432 discloses anti proliferative effects of dopamine receptor antagonists against acute myeloid leukemia. The use of dopamine receptor antagonists for treating other malignancies is not supported.

WO 2013/143000 provides combinations of the multi dopamine receptor antagonist thioridazine and the leukemic therapeutic cytarabizine as beneficial in the therapy of acute myeloid leukemia. The document in particular emphasises the beneficial use against leukemia of drugs that target multiple dopamine receptors at the same time, such as thioridazine.

Irrespective of the aforementioned prior art, the expression of dopamine receptors in various malignancies is highly controversially discussed. Melanoma cells for example do not appear to express the dopamine D2 receptor, which was shown by Boeni R, et al. (Dermatology. 1996). For DRD2 it is even known that reduced expression of the receptor is associated with the occurrence of colorectal cancer (Gemignani F et al: "Polymorphisms of the dopamine receptor gene DRD2 and colorectal cancer risk.", Cancer Epidemiol Biomarkers Prev. 2005 July; 14(7): 1633-8).

Other studies revealed that supporting expression and activity of dopamine receptors, in particular of DRD2, is beneficial in the treatment of small cell lung cancer (Senogles S: "D2 dopamine receptor-mediated antiproliferation in a small cell lung cancer cell line, NCI-H69." Anticancer Drugs. 2007 August; 18(7):801-7). DRD2 agonists were shown to be applicable in cancer treatments. After either dopamine or quinpirole (DRD2 agonist) treatment, the cancer cell viability decreased significantly (An J J et al.: "Anti-proliferative effects and cell death mediated by two isoforms of dopamine D2 receptors in pituitary tumor cells." Mol Cell Endocrinol. 2003 Aug. 29; 206(1-2):49-62).

In view of the above described limited options for a successful treatment of pancreatic cancer in the art, providing new pancreatic cancer targets are desperately needed. Thus, the objective of the present invention is to provide a novel pancreatic cancer target, and in particular novel therapeutic strategies to treat or prevent pancreatic cancer. Another object of the invention intends to provide alternative diagnostic methods that allow diagnosing the occurrence of pancreatic cancer in a subject, or at least help to establish a pancreas cancer diagnosis.

The above problem is solved in a first aspect by an antagonist of a dopamine receptor for use in the treatment of pancreatic cancer or chronic pancreatitis. Preferred in the context of the present invention is an antagonist of dopamine receptor D2 (DRD2).

In context of the present invention it was found that the dopamine receptor DRD2 is significantly expressed in chronic pancreatitis as a strong risk factor for pancreatic cancer and tumor cells of the pancreatic ductus. This is in view of the mixed reports regarding the expression of dopamine receptors in several malignancies very surprising—indeed dopamine receptors in pancreatic cancers provide in accordance with the present invention a promising new pancreatic cancer target for the development of new treatment regimens which will be described in more detail herein below. More importantly, it was observed that inhibiting the expression of DRD2 using a shRNA construct induced cell death specifically in cancer cells. This effect could be reproduced using exemplary small molecular antagonists of DRD2, namely pimozide or L-741,626. Pimozide has a high affinity to DRD2 and blocks the proteins function efficiently. L-741,626 is a very selective inhibitor of DRD2, and also blocks efficiently DRD2 activity. Thus, the present invention provides proof that inhibition of dopamine receptors in the pancreas at various levels, both protein expression, and inhibition of the activity of expressed protein, is beneficial for a pancreatic cancer treatment. Both inhibition of the expression and the activity of DRD2 yielded into a significant toxic effect in cancer cells. Moreover, cell-growth inhibitory function of DRD2 antagonist on pancreatic cancer cells is considerably stronger than on normal fibroblast cells. These results are in agreement with the herein disclosed observations that protein levels of DRD2 are different when comparing pancreatic ductal cancer versus normal ductal pancreas tissue in this study. Therefore, the invention provides a teaching that various kinds of dopamine receptor antagonists, in particular antagonists of DRD2, can be applied in the therapy of a patient suffering from a pancreatic cancer or pancreatitis. Since pancreatitis and specifically chronic pancreatitis (CP) is known to be a condition observed in advance of cancer development in the pancreas, the compounds and methods of the invention can equally be used for pancreatitis and preferably chronic pancreatitis.

The term "antagonist of a dopamine receptor" refers to a compound that produces any detectable or measurable reduction in the expression, function or activity of one or more dopamine receptors. The terms "antagonist" and "inhibitor" shall be used interchangeably herein. In one embodiment, the dopamine receptors (DR) are selected from DRD1, DRD2, DRD3, DRD4 and DRD5, however, in the context of the present invention antagonists of DRD2 are preferred. Whether or not a candidate compound or molecule qualifies as an antagonist of a dopamine receptor in accordance to the invention can be easily assessed by the skilled person using standard procedures in the art, for example by measuring dopamine receptor enzymatic activity, or using dopamine receptor specific reporter assays in cell culture models. Expression of dopamine receptor can be assessed by quantitative RT-PCR or immunohistochemically, using antibodies against the respective dopamine receptor. DRD2 antibodies are for example available from Santa Cruz Biotechnology® (Cat No. sc-5303). In order to assess the activity or function of DRD2, one possibility is to use DRD2 ligand binding assays, that are well known in the art and qualify for high throughput approaches (for example as presented by Mathias G et al. SBS 17th Annual Conference, April 2011, Orlando, USA).

The term "chronic pancreatitis" refers to a condition of the pancreas characterized by a long-standing inflammation of the pancreas that alters the organ's normal structure and functions. It can present as episodes of acute inflammation in a previously injured pancreas, or as chronic damage with persistent pain or malabsorption. Chronic pancreatitis is known to be a first stage for the development of pancreatic cancers.

In certain embodiments of the invention the antagonist of a dopamine receptor is selected from the group consisting of an RNAi construct, an antibody and a small molecule.

An RNAi (RNA interference) construct usually comprises a nucleotide sequence that is complementary to the nucleotide sequence of the mRNA of a dopamine receptor. Such RNAi constructs are well known in the art and can be provided as short hairpin RNAs (shRNA) or small interfering RNAs (siRNA).

Preferred RNAi constructs in accordance with the invention are lentiviral shRNA targeting DRD2, preferably which can be found at http://www.sigmaaldrich.com/life-science/functional-genomics-and-rnai/shrna/library-information.html or http://www.broad.mit.edu/genome_bio/trc/rnai.html. Most preferred are the vectors TRCN0000011342 and TRCN0000011343.

"RNA interference" refers to sequence-specific, post-transcriptional gene silencing of a selected target gene. The RNAi agents in the context of the present invention, preferably, reduce the expression of a dopamine receptor, or a dopamine receptor signaling gene by degradation of RNA transcribed from said dopamine receptor signaling gene (target RNA) or by inhibition of translation of said target RNA. Target RNAs preferably are mRNAs coding for dopamine receptor signaling components, however, any type of RNA is encompassed by the RNAi methods of the invention. It is to be understood that silencing as used herein does not necessarily mean the complete abolishment of gene expression in all cases. RNAi, preferably, reduces gene expression by at least 50%, at least 60%, at least 70%, at least 80%, at least 90%, at least 95%, at least 98%, or at least 99% as compared to the expression level in a reference without RNAi.

RNAi requires in the cell the presence of double stranded RNAs (dsRNAs) that are homologous in sequence to the target RNAs. The term "dsRNA" refers to RNA having a duplex structure comprising two complementary and antiparallel nucleic acid strands. The RNA strands forming the dsRNA may have the same or a different number of nucleotides, whereby one of the strands of the dsRNA can be the target RNA. It is, however, also contemplated by the present invention that the dsRNA is formed between two sequence stretches on the same RNA molecule.

RNAi may be used to specifically inhibit expression of dopamine receptor, or dopamine receptor signalling genes of the present invention in vivo. Accordingly, it may be used for therapeutic approaches to treat pancreatic cancers which are accompanied with an altered expression of at least one of the dopamine receptor signaling genes of the present invention. For such therapeutic approaches, expression constructs for siRNA or shRNA may be introduced into target cells of the host which suffer from dopamine receptor gene expression. Accordingly, siRNA may be combined efficiently with other therapy approaches.

Methods relating to the use of RNAi to silence genes in animals, including mammals, are known in the art (see, for example, Hammond et al. (2001), Nature Rev. Genet. 2, 110-119; Bernstein et al. (2001), Nature 409, 363-366; WO 9932619; and Elbashir et al. (2001), Nature 411: 494-498).

As used herein, the term "RNAi construct", preferably, refers to a shRNA, siRNA or a miRNA construct as specified herein. The RNAi construct of the present invention is of sufficient length and complementarity to stably interact with the target RNA, i.e. it comprises at least 15, at least 17, at least 19, at least 21, at least 22 nucleotides complementary to the target RNA. By "stably interact" is meant interaction of the RNAi construct or its products produced by the cell with a target RNA, e.g., by forming hydrogen bonds with complementary nucleotides in the target RNA under physiological conditions.

Small molecule antagonists of the invention are preferably selected from the group consisting of acetopromazine maleate salt (dopaminergic antagonist), amisulpride (D2 and D3 receptor antagonist), amoxapine (dopamine-reuptake inhibitor), azaperone (dopaminergic receptor antagonist), benperidol (dopamine antagonist), benzo[a]phenanthridine-10,11-diol, 5,6,6a,7,8,12b-hexahydro-, trans-[CAS] (D1 ligand), bromopride (dopamine antagonist), bromperidol (dopamine antagonist), chlorpromazine hydrochloride (D2 antagonist), clomipramine hydrochloride (chlorpromazine derivative), disulfiram (dopamine beta-hydroxylase inhibitor), DO 897/99 (D3 antagonist), domperidone (dopamine antagonists), droperidol (D2 (dopamine receptor) antagonist), ethopropazine hydrochloride (thioridazine derivative), fluperlapine (D2 (dopamine receptor) antagonist), fluphenazine dihydrochloride (D1&D2 antagonist), GBR 12909 dihydrochloride (dopamine reuptake inhibitor), haloperidol (dopamine antagonist D2), hydrastinine hydrochloride (dopamine receptor blocker), indatraline (potent D antagonist), itopride (dopamine D2 receptors and ACE inhibition), levosulpiride (D2, D3, & D4 antagonist), loxapine succinate (dopamine antagonist/D2, D4), mesoridazine (D2 antagonist), mesoridazine besylate (D antagonist), methotrimeprazine maleat salt (thioridazine derivative), metixene hydrochloride (thioridazine derivative), molindone hydrochloride (dopamine receptor antagonist), nafadotride (D3 antagonist), nomifensine maleate (dopamine uptake inhibitor), olanzapine (D1&D2 antagonist), perospirone HCl (D2&D4 antagonist), perphenazine (D1 & D2 antagonist), phenothiazine (thioridazine derivative), pimozide (dopamine antagonist), piperacetazine (thioridazine derivative), prochlorperazine (thioridazine derivative), prochlorperazine dimaleate (dopamine antagonist), promazine hydrochloride (dopamine receptor antagonist), promethazine hydrochloride (thioridazine derivative), quetiapine (dopamine and serotonin receptors antagonist), quetiapine hemifumarate (D2 antagonist), R(+)-SCH-23390 hydrochloride (D1 antagonist), raclopride (D2 antagonist), remoxipride hydrochloride (dopaminergic antagonist), risperidone (D1 & D2 antagonist), S(−)eticlopride hydrochloride (dopamine receptor antagonist), sertindole (dopamine D2/serotonin, 5-HT2 receptor antagonist), SKF 83566 (D1 antagonist), spiperone (D2 antagonist), sulpiride (D2 antagonist), sulpiride (D2 &

D3 antagonist), thiethylperazine malate (thioridazine derivative), thioproperazine dimesylate (D1 & D2 antagonist), thioridazine hydrochloride (thioridazine derivative), trifluoperazine (D2 antagonist), triflupromazine hydrochloride D1 & D2 antagonist, trimeprazine tartrate (thioridazine derivative), trimethobenzamide hydrochloride (D2 antagonist), ziprasidone hydrochloride (dopamine D2/serotonin 5-HT2 antagonist), zotepine (dopamine D2/serotonin 5-HT2 antagonist).

Particular preferred antagonists of the invention are selected from the group consisting of pimozide and L-741,626, L-741,626 having the chemical structure of formula II:

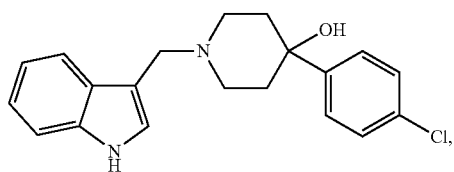

(II)

and preferably is pimozide. Other antagonists of the invention may be selected from the group consisting of aceprometazine, ecopipam, EEDQ, FLB 457, flupenthixol decanoate, hydroxyzine, iodobenzamide, levomepromazine, tiapride, and tiapride hydrochloride.

The term "antibody" as used in this specification refers to a molecule from the subgroup of gamma globulin proteins which is also referred to as the immunoglobulins (Ig). Antibodies can, preferably, be of any subtype, i.e. IgA, IgD, IgE, IgM or, more preferably, IgG. Antibodies against dopamine receptor polypeptides of the invention can be prepared by well-known methods using a purified polypeptide or a suitable fragment derived therefrom as an antigen. A fragment which is suitable as an antigen may be identified by antigenicity determining algorithms well known in the art. Such fragments may be obtained either by proteolytic digestion from dopamine receptor polypeptides or may be synthetic peptides. Preferably, the antibody of the present invention is a monoclonal antibody, a polyclonal antibody, a single chain antibody, a human or humanized antibody or primatized, chimerized or fragment thereof. Also comprised as antibodies of the present invention are a bispecific or a trispecific antibody, a synthetic antibody, an antibody fragment, such as Fab, Fv or say fragments etc., or a chemically modified derivative of any of these. An antibody of the present invention preferably binds specifically (i.e. does not cross react with other polypeptides or peptides) to one dopamine receptor, preferably DRD2. Specific binding can be tested by various well known techniques.

The term "inhibitory antibody" relates to an antibody inhibiting the activity of a dopamine receptor referred to in accordance with the present invention. Said inhibition preferably is caused by binding of the inhibitory antibody to an active center or to an interaction site of a dopamine receptor of the invention, causing an inhibition of dopamine receptor signaling in the cell treated with said inhibitory antibody. The person skilled in the art knows means and methods to obtain inhibitory antibodies to specific proteins, like e.g. the method proposed by Rosen and Koshland (1988), Anal. Biochem. 170(1), 31-37. It is to be understood that inhibiting as used herein does not necessarily mean the complete abolishment of activity in all cases Inhibitory antibodies, preferably, reduce dopamine receptor signaling by at least 10%, at least 20%, at least 30%, at least 40%, or at least 50% as compared to a reference.

The term "cancer" as referred to in the present invention relates to any neoplastic disease which is characterized by abnormal and uncontrolled cell division causing malignant growth or tumor. Cancer cells, unlike benign tumor cells, exhibit the properties of invasion and metastasis and are highly anaplastic. In some embodiments, said cancer is a solid tumor (i.e. essentially solid neoplasmic growth, with low liquid content that is other than a cyst) or tumor metastasis (i.e. at its metastatic stage of disease).

The term "treatment of cancer", or "treatment of pancreatic cancer" as used in the context of the present invention relates to any kind of change in the disease state or condition of a subject in need thereof including any degree of: a decrease in tumor size; decrease in rate of tumor growth; stasis of tumor size; decrease in the number of metastasis; decrease in the number of additional metastasis; decrease in invasiveness of the cancer; decrease in the rate of progression of the tumor from one stage to the next, inhibition of tumor growth in a tissue of a mammal having a malignant cancer, control of establishment of metastases, inhibition of tumor metastases formation, regression of established tumors as well as decrease in the angiogenesis induced by the cancer. The term "treatment of cancer" can also refer to prophylactic treatment, such for example the prevention of cancer reoccurs after previous treatment (including surgical removal) and prevention of cancer in an individual prone (genetically, due to life style, chronic inflammation and so forth) to develop cancer.

The term "administering" or its other lingual forms as used in the context of the present invention relates to the path by which a pharmaceutically active component, a drug, fluid or other substance is brought into contact with the body of a subject. The pharmaceutical composition is transported from the site of entry to the part of the body where its action is desired to take place, according to one embodiment of the present invention, said administering may be achieved via any medically acceptable means suitable for a pharmaceutical composition of the invention or any component thereof, including oral, rectal, vaginal, nasal, topical, transdermal, or parenteral (including subcutaneous, intramuscular, intrasynovial, intraperitoneal, intradermal and intravenous) administration.

In therapeutic applications, the dosages and administration schedule of components of a pharmaceutical composition of the invention may vary depending on the component, the age, weight, and clinical condition of the recipient patient, and the experience and judgment of the clinician or practitioner administering the therapy, among other factors affecting the selected dosage. Generally, the dose and administration scheduled should be sufficient to result in slowing and/or regressing, the growth of the tumor(s) and may also cause complete regression of the cancer. In some cases, regression may be monitored via direct imaging (e.g. MRI) or by a decrease in blood levels of tumor specific markers. An effective amount of the pharmaceutical composition is that which provides a medical benefit as noted by the clinician or other qualified observer. Regression of a tumor in a patient is typically measured with reference to the diameter of a tumor. Decrease in the diameter of a tumor indicates regression. Complete regression is also indicated by failure of tumors to reoccur after treatment has stopped. The present invention allows for the administration of a pharmaceutical composition of the present invention, either prophylactically or therapeutically or in the context of adjuvant or neo-adjuvant treatment.

When provided prophylactically, antagonists, combinations or compositions of the invention may be administered in advance of any symptom. Prophylactic administration of pharmaceutical compositions may serve to prevent or inhibit cancer or chronic pancreatitis. A pharmaceutical composition of the invention may prophylactically be administered to a patient with, for example, a family history of pancreatic cancer or chronic pancreatitis. The risk for developing pancreatic cancer or chronic pancreatitis may be determined by measuring levels of pancreatic cancer or chronic pancreatitis marker proteins in the biological fluids (i.e. blood, urine) or pancreatic tissue of a patient or by genetic markers.

Therefore in one embodiment of the invention said treatment of pancreatic cancer or chronic pancreatitis comprises the administration of said antagonist to a subject suffering from pancreatic cancer or chronic pancreatitis. Preferably a therapeutically sufficient amount of said antagonist is administered to said subject.

The term "subject" in context of the invention preferably refers to a mammal, preferably a human.

Preferred embodiments of the invention pertain to pimozide for use in the treatment of pancreatic cancer or chronic pancreatitis. In this regard said treatment with pimozide comprises an administration of pimozide in about 0.01 to 5 mg/kg body weight/day, preferably 0.1 to 0.5 mg/kg body weight/day, most preferably in about 0.2 mg/kg body weight/day, preferably wherein pimozide is applied orally.

Other preferred embodiments of the invention pertain to pancreatic cancer which is primary pancreatic cancer, metastatic pancreatic cancer, refractory pancreatic cancer, and/or cancer drug resistant pancreatic cancer. A pancreatic cancer of the invention may be an adenocarcinoma, preferably ductal adenocarcinoma.

Preferred alternative embodiments for all aspects of the invention pertain to only pancreatic cancer, and not chronic pancreatitis.

Surprisingly it was found that the inhibition of dopamine receptors, such as DRD2, not only inhibited the tumor cell viability, but also had a significant impact—a reduction—on the migration capacity of tumor cells. Therefore, the antagonists of dopamine receptors in accordance with the present invention are useful for the specific treatment of metastatic tumors, or for the prevention of the development of pancreatic cancer metastasis.

In one further embodiment the afore described antagonist for use in the treatment of pancreatic cancer or chronic pancreatitis can be administered in combination with at least one additional anti-cancer drug, which preferably is known to be effective against pancreatic cancer, such as gemcitabine.

In context of the present invention it was surprisingly found that using a dopamine receptor antagonist such as pimozide can enhance the anti-proliferative activity of other pancreatic cancer drugs such as gemcitabine. In preferred embodiments gemcitabine is administered by the intravenous route. Dose ranges from 0.5 to 2, preferably 1-1.2 g/m2 of body surface area. Drug doses can be adjusted according to Chu E., DeVita V. T., "Physicians' Cancer Chemotherapy Drug Manual, 2007", Jones & Bartlett, 2007.

As already disclosed before, the antagonist in accordance with the invention may be an inhibitor of the activity of said dopamine receptor, or an inhibitor of the expression of said dopamine receptor.

In another aspect the above problem is solved by providing a combination for use in the treatment of pancreatic cancer or chronic pancreatitis, comprising an antagonist of a dopamine receptor as described above, together with at least one additional anti-cancer drug.

The combination of the present invention provides advantages to state of the art cancer or chronic pancreatitis treatments. The examples show that the combination of a dopamine receptor antagonist enhances the activity of another pancreatic cancer drug. Therefore, the combination will have the advantage that the individual combination compounds can be used in lesser amounts which reduces the occurrence of adverse effects. Also the combinations of the invention provide synergistic activity as the sum of their individual effects is lower than the effect of the combination. Therefore, the combination of the invention in a preferred embodiment of this aspect comprises the combination compounds in synergistically effective amounts.

In one preferred embodiment of the invention said at least one additional anti-cancer drug to be used in the combination is gemcitabine.

Yet another aspect of the invention pertains to a pharmaceutical formulation (or composition which means the same in this context), comprising an antagonist of a dopamine receptor as described above, or a combination as described above, optionally together with pharmaceutically acceptable excipients and/or carriers.

The terms "pharmaceutical formulation", "pharmaceutical composition" and "medicament" are used interchangeably herein, and comprise the antagonists or combinations of the present invention and optionally one or more pharmaceutically acceptable carrier and/or excipient. The compounds of the present invention can be formulated as pharmaceutically acceptable salts. Acceptable salts comprise acetate, methylester, HCl, sulfate, chloride and the like. The medicaments are, preferably, administered topically or systemically. Suitable routes of administration conventionally used for drug administration are intratumoral, peritumoral, oral, intravenous, or parenteral administration as well as inhalation. However, depending on the nature and mode of action of the compound, the medicaments may be administered by other routes as well. For example, polynucleotide compounds may be administered in a gene therapy approach by using viral vectors, viruses or liposomes.

The present invention provides in a further aspect also a method for treating or preventing pancreatic cancer or chronic pancreatitis in a subject in need of such a treatment, the method comprising the administration of an antagonist of a dopamine receptor as described above, or a combination as described above.

The term "prevention" or "preventing" refers to retainment of health with respect to the disease (pancreatic cancer or chronic pancreatitis) or the symptoms referred to herein for a certain period of time in a subject. It will be understood that the said period of time is dependent on the amount of the drug compound which has been administered and individual factors of the subject. It is to be understood that prevention may not be effective in all subjects treated with the compound according to the present invention. However, the term requires that a statistically significant portion of subjects of a cohort or population are effectively prevented from suffering from a disease or the symptoms referred to herein. Preferably, a cohort or population of subjects is envisaged in this context which normally, i.e. without preventive measures according to the present invention, would develop a disease or symptoms as referred to herein. Whether a portion is statistically significant can be determined without further ado by the person skilled in the art using various well known statistic evaluation tools discussed above. Preferably, prevention shall be effective for at least 60%, at least 70%, at least 80%, or at least 90% of the subjects of a given cohort or population.

Furthermore described is the use of an antagonist of a dopamine receptor mentioned above, for the manufacture of a medicament for treating pancreatic cancer or chronic pancreatitis.

The problem posed by the prior art is further solved by a diagnostic method for detecting chronic pancreatitis and/or pancreatic tumor cells in a subject. The method of the invention comprises the steps of:

a. Providing a biological sample derived from the pancreas of said subject, b. Detecting the presence or absence of a dopamine receptor (preferably DRD2) in said biological sample, wherein the presence of said dopamine receptor (preferably DRD2) in said biological sample is indicative for the presence of pancreatic tumor cells and/or chronic pancreatitis.

The expression of dopamine receptors, namely DRD2, in pancreatic cancer tissue and chronic pancreatitis is for the first time described herein. Therefore, dopamine receptors, and DRD2 in particular, provide a novel biomarker for the diagnosis of the presence of cancer cells of pancreatic origin. In addition, the identification of dopamine receptor expression in a sample from a subject does not only allow for the diagnosis of pancreatic cancer, it also provides the clinical practitioner with the information that this cancer may be treated with antagonists of dopamine receptors. Diagnosing in context of the herein describe invention therefore also relates to the assessment of treatment options for a pancreatic cancer patient.

In a preferred embodiment of the method of the invention said biological sample is a pancreatic tissue sample, preferably a pancreatic ductal tissue sample. For example this sample may be an immersion fixed paraffin embedded tissue sample.

The method of the invention in preferred embodiments furthermore includes in step b. that DRD2 is detected directly, for example immunohistochemically, or indirectly by detecting DRD2 mRNA expression.

The method of the invention is preferably an ex-vivo or in-vitro method.

"Subjects" in this context are preferably a mammal, preferably a human. The subject is maybe suspected to carry pancreatic cancer or suffer from chronic pancreatitis. In this context the method of the invention seeks to establish a first diagnosis of the presence of pancreatic cancer or chronic pancreatitis. Also the method includes scenarios where the tissue of a resected pancreatic tumor is assayed for the presence or expression of a dopamine receptor antagonist. In this regard, although the diagnosis of pancreatic cancer or chronic pancreatitis is already established, the presence or expression of a dopamine receptor is indicative for a successful treatment with an antagonist of a dopamine receptor. The above general descriptions regarding the first and second aspects of the invention of course also apply for the diagnostic aspects.

Finally provided is in another aspect a diagnostic kit for detecting pancreatic tumor cells or chronic pancreatitis, comprising means for performing a method as described herein above, preferably means for the detection of DRD2, such as nucleic acid probes or antibodies, together with appropriate buffers and solutions. Such means are well known to the person of skill.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Immunohistochemical analysis of DRD2 levels in clinical tissues. Representative examples of DRD2 expression in duct part of normal pancreas (A), CP (B) and PDAC (C) in clinical tissues using anti-DRD2 are shown. Normal ductal cells are almost DRD2 negative, CP lesion and PDAC represented with moderate and strong DRD2 expression, respectively.

Figure 2:
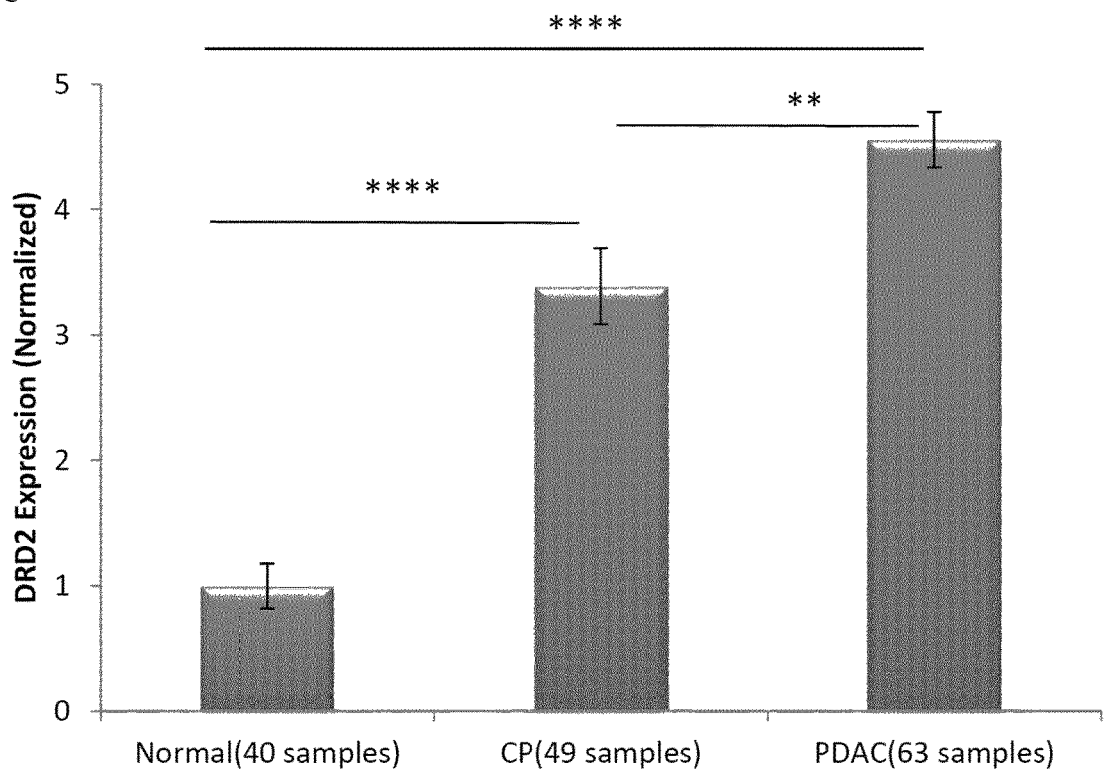

FIG. 2: Immunohistochemical analysis of DRD2 levels using a large number of clinical tissues, Tissue Microarray (TMA). Distribution of DRD2 expression in clinical tissues revealed its high expression in PDAC and CP in comparison with mild positivity in pancreatic ducts normal samples.

Figure 3:
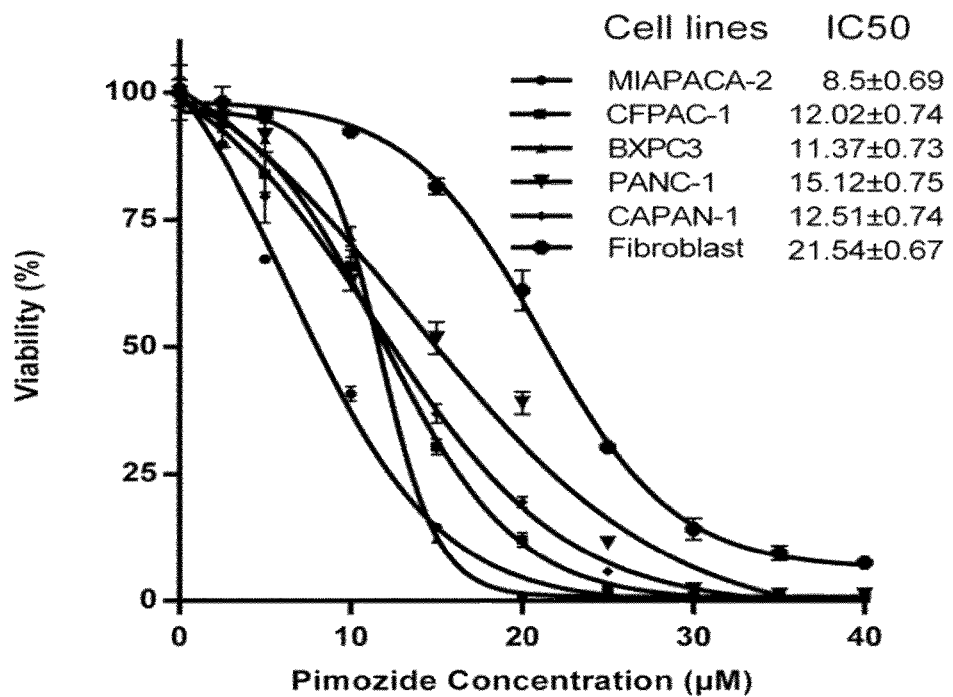
Figure 3:
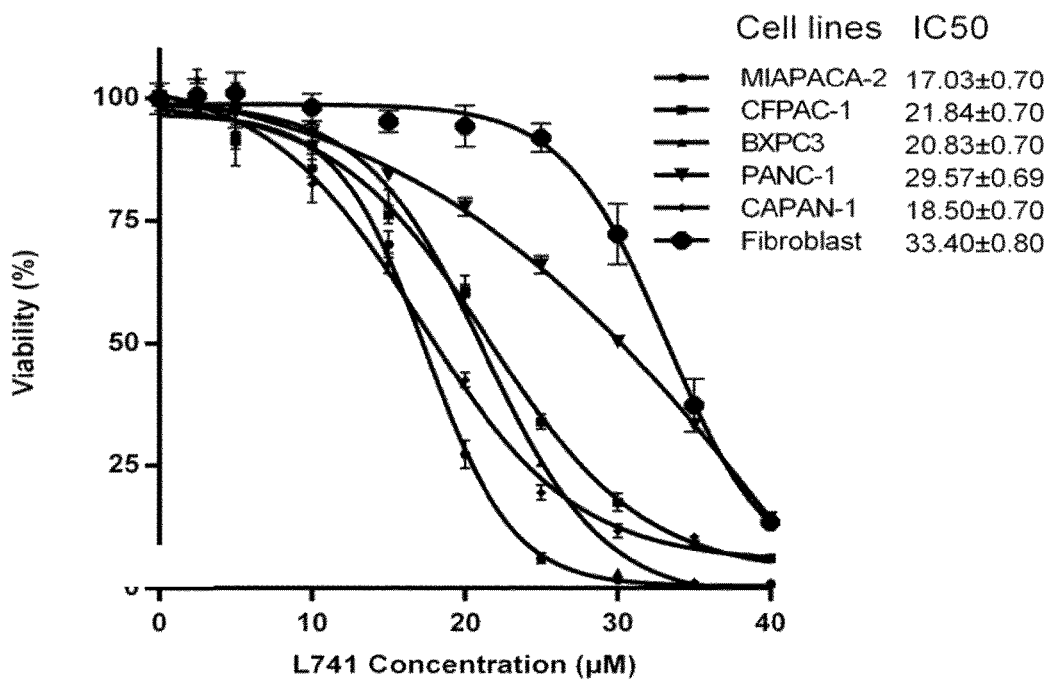

FIG. 3: Dose dependent toxicity effect of pimozide and L741 on PDAC cell. A) PANC-1, CFPAC-1, CAPAN-1, MIAPACA-2, BXPC-1 and fibroblast cells were seeded for 24 h and were exposed to increasing concentration of pimozide and vehicle for 72 h. B) The same procedure was followed for treatment of cancer cell lines with L741. Cell viability was characterized using a SRB assay. Values are the mean+−SD of six independent experiments.

Figure 4:
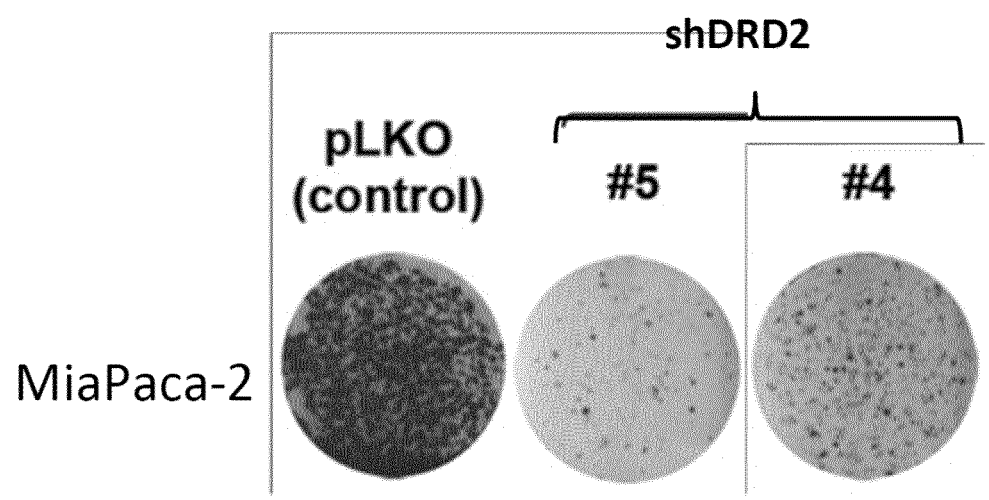
Figure 4:
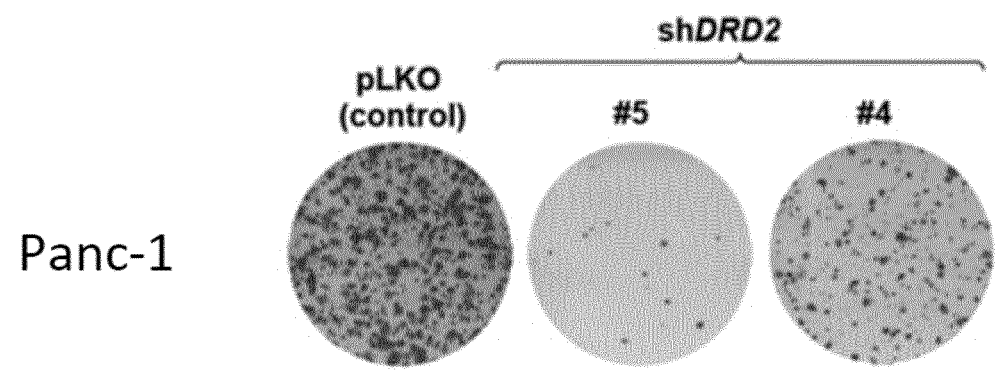

FIG. 4: Independent shRNAs targeting DRD2 sensitizes pancreatic cancer cells to their anti-tumor effects. Colony formation assay of MIAPACA-2 (A) and PANC-1(B) cells that express pLKO as a control or independent lentiviral shDRD2 vectors (#4 and #5) were performed. The cells were fixed, stained, and photographed after 10 (pLKO) or 28 days (shDRD2).

Figure 5:
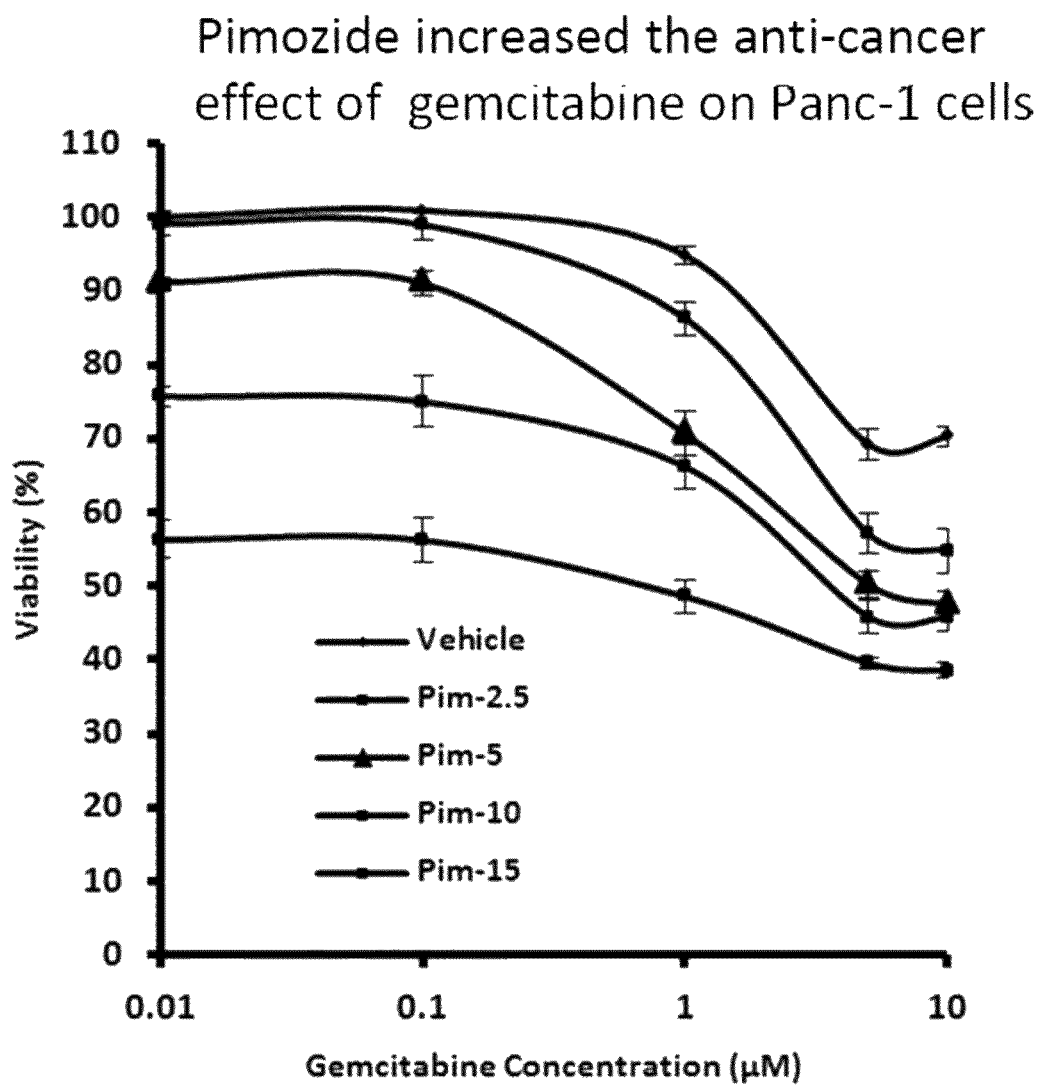

FIG. 5: Effect of increasing concentrations of GEM and/or pimozide on PANC-1 cell growth. A) PANC-1 was seeded for 24 h and was exposed to different concentration of gemcitabine, pimozide or combination of them for 72 h. Cell viability was characterized using a SRB assay. Values are the mean+−SD of six independent experiments.

Figure 6:
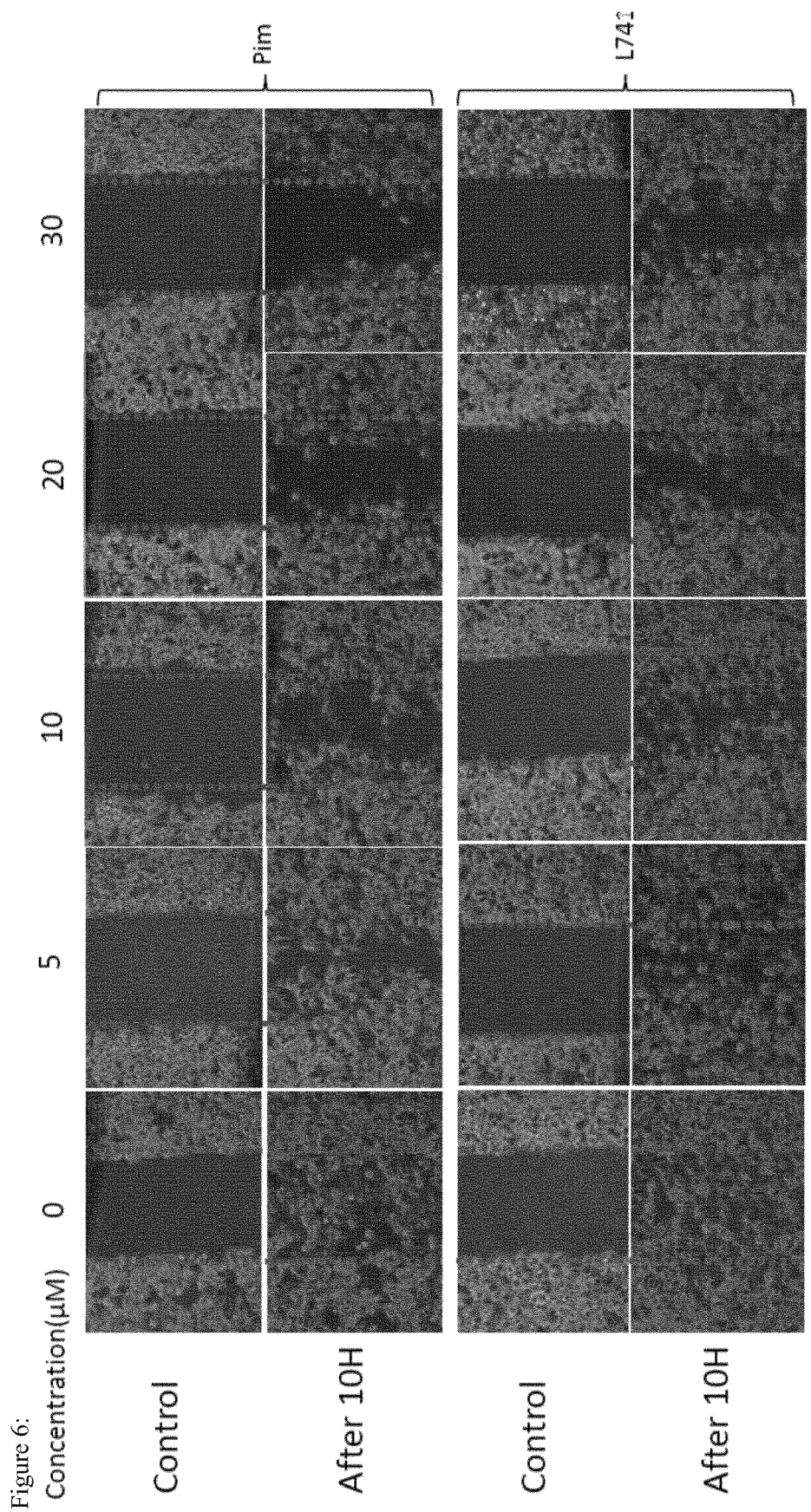

FIG. 6: Dose dependent inhibitory effect of pimozide and L741 on migration of PDAC cells in wound healing assay. PANC-1 cells were plated in the chamber were already attached in 12 well plate and allowed to grow for 24 h. Then, a wound was made in the confluent monolayer by removing the chamber. Cells were exposed to increasing concentration of A) pimozide or B) L741 and vehicle for 10 h. Wound gap closure was measured for each drug concentration by comparing the gap at time 0 h to the one at the time 10 h when the gap closed in negative control and normalized to untreated condition.

Figure 7:
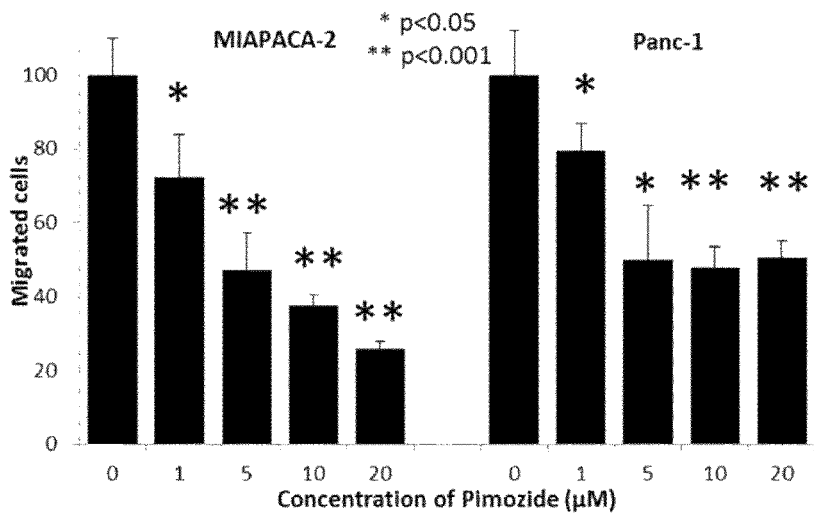

FIG. 7: Dose dependent inhibitory effect of pimozide on migration of PDAC cells using Boyden chamber. A) MIAPACA-2 cells were platted on transwells and exposed to increasing doses of pimozide for 4 h. Migrated cells were measured and normalized to their controls. Values are the mean+−SD of four replicate. B) The dose dependent inhibitory effect of pimozide on PANC-1 cells migration was assessed as described above using Boyden chamber.

Figure 8:
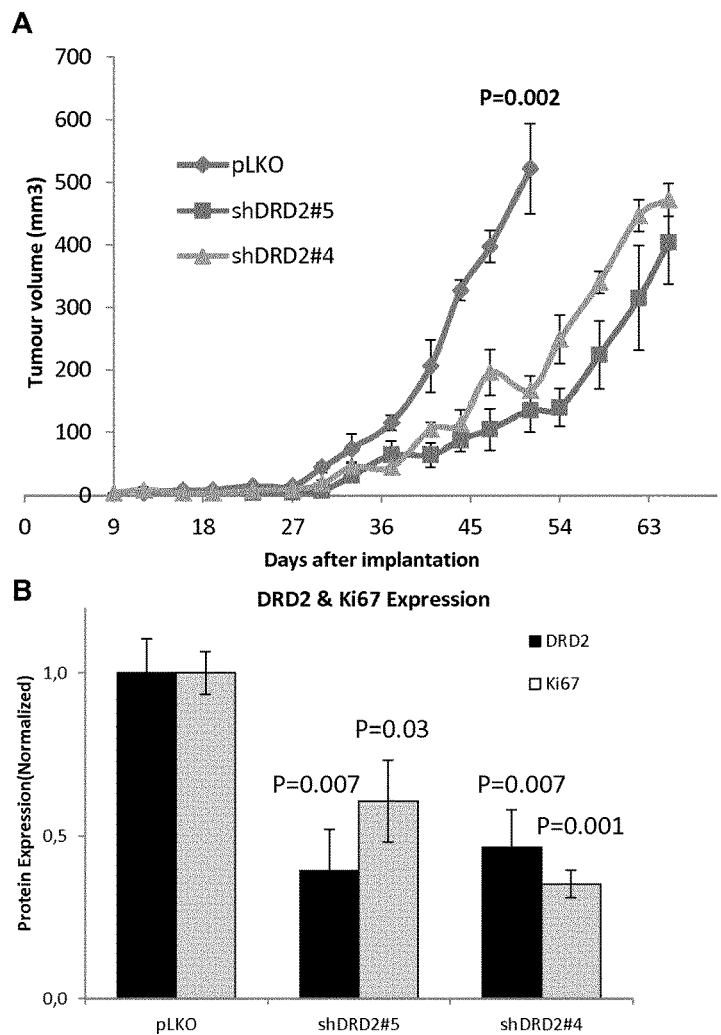

FIG. 8: Inhibition of tumor growth in vivo. A) Mice implanted with PANC-1 cell and expressing shDRD2 or control constructs were monitored for tumor growth. B) Relative protein expression of DRD2 and Ki67.

EXAMPLES

Materials and Methods

Study Population and IHC

Tissue microarray (TMA) slides of human pancreatic tissue samples were included with 63 cases of Pancreatic Ductal Adenocarcinoma (PDAC), 49 cases of chronic pancreatitis (CP) and 40 of healthy pancreatic tissues (Normal) from non-cancer patients.

IHC on TMA slides pursued with boiling the samples two times in citrate buffer (10 mM) for 10 min and suppressing of peroxidase with the solution of H2O2 (3%) in 30% methanol. Slides were incubated overnight with a dilution of anti-DRD2 antibody (1:50) and IgG2b (1:375) as a negative control at 4° C. TBS-T buffer solution was used to wash antibodies out from the unbounded target proteins and then, slides exposed to the anti-mouse HRPO conjugated secondary antibody at room temperature for 1 h. Diaminobenzidine peroxidase substrate was used to yield intense dark brown color for detection of target protein and Mayer's hematoxylin solution to stain the nuclei. Sections were scanned with ScanScope GL System (Aperio Technologies, Vista, USA) and two pathologists independently checked the results to detect ductal structures and quality of staining in the samples.

Cell Lines and Treatment Reagents

Five pancreatic ductal cancer cell lines with various degree of differentiation were obtained from American Type Culture Collection (Rockville, USA) and Normal Human Dermal Fibroblasts (NHDF) obtained from PromoCell-.BXPC-3(moderately differentiated) as well as poorly differentiated human pancreatic cancer cell lines, panc-1 and Miapaca-2, have been established from primary tumor. CAPAN-1 and CFPAC-1 which represent well differentiated cell lines was isolated from liver metastasis of pancreas adenocarcinoma. All cell lines contain mutation in P53 whereas K-ras mutation reported in all with the exception of BxPc3. BRCA2 mutation just reported in CAPAN-1 cells.

MiaPaCa2 and Panc1 were maintained in DMEM medium, NHDF and CFPAC1 in IMDM medium and BxPc3 and CAPAN1 in RPMI 1640 medium supplemented with 10% (v/v) heat-inactivated fetal bovine serum, 100 µg/ml streptomycin and 100 U/ml penicillin. They were maintained in humid environment with 5% CO2 at 37° C.

Pimozide (DRD2 antagonist), L-741,626 (selective DRD2 antagonist) was purchased from Sigmaaldrich. They suspended in DMSO to make a stock solution and stored at −20° C. A stock solution of gemcitabine (Sigma Aldrich) C in water stored at −20° as well. For non-specific solvent effect on cells, same concentration of DMSO was used as a control and its concentration did not overpass 0.2% in all treatments.

antagonists or gemcitabine were added on them. After 72 h of treatment, cell medium of each wells replaced with 200 µL of cell fixative reagent 10% (w/v) tricholoroacetic acid (TCA). After incubation of plate in 4° C. for 3 h, the fixed Cells washed with water and allow them to dry in 37° C. for 1 h. 50 µL of 0.4% (w/v) SRB staining solution (sulforhodamine B solved in 0.1% acetic acid) was added in each well to completely cover the cells. Experiment was followed by washing the cells from unbounded SRB after 30 min of incubation in room temperature with 0.1% acetic acid. Cells were then dried and SRB which was bound with mammalian cell protein dissolved with 100 µL of 10 mM Tris-base solution (TBS). Cell viability was specified by using plate reader (TECAN) with measuring of absorbance at 570 and 650 nm(background) in treated or untreated 96 well plate.

For colony formation assay, cells infected with lentiviral supernatants were trypsinized and plated in a 6 well plate as single cells (1000 cells per well). Cells were allowed to attach 24 h and then they were treated with puromycin. Media was removed every 4 days, the cells washed once and fresh media added. Colony formation assays continued for an additional 10 (for pLKO) or 28 days (for DRD2$^{KD}$). Upon colony formation, the medium was aspirated and the cells washed with PBS. Afterward, the cells were fixed for 10 min by adding 100% methanol. The methanol was then removed and replaced with 0.1% (v/v) crystal violet staining solution for 1 h in order to visibly colonies.

Plasmids and Viral Transduction

All lentiviral shRNA vectors were retrieved from the arrayed Mission® TRC genome-wide shRNA collections purchased from Sigma-Aldrich Corporation. Additional information about the shRNA vectors can be found at http://www.sigmaaldrich.com/lifescience/functional-genomics-and-rnai/shrna/library-information.html or http://www.broad.mit.edu/genome_bio/trc/rnai.html, using the TRCN number. The following lentiviral shRNA vectors targeting DRD2 were used: TRCN0000011342 and TRCN0000011343. HEK293T cells were used as producers of lentiviral supernatants and the calcium phosphate method was used for the transfection of this cells which described at http://www.broadinstitute.org/rnai/public/resources/protocols. Infected cells by lentiviral supernatants were selected for successful lentiviral integration using 2 mg/ml of puromycin.

TABLE 1

Used cell lines and their origin

| Cell Lines | K-ras | BRCA2 Mut | P53 Mut | Cell Source | Cell type | Differentiation |
|---|---|---|---|---|---|---|
| BXPC-3 | − | − | + | Primary tumor | Ductal | Moderate |
| CAPAN1 | + | + | + | Liver metastasis | Ductal | Well |
| CFPA-1 | + | − | + | Liver metastasis | Ductal | Well |
| MIAPACA-2 | + | − | + | Primary tumor | Ductal | Poor |
| PANC-1 | + | − | + | Primary tumor | Ductal | Poor |
| Fibroblast | − | − | − | Primary cell | Normal | — |

Sulforhodamine B Cytotoxicity and Colony Formation Assay

Sulforhodamine B sodium salt (sigma) was used to assess cell viability and IC50 determination of pancreatic cancer cells. Briefly, cells were placed in 96 well plates and allowed to settle for 24 h. Cell medium was aspirated and fresh medium with or without different increasing dosage of Wound Healing Assay for Cell Migration PANC-1 cells were seeded into the 35 mm-Dish Culture-Silicon Insert frames from Ibidi where already attached to the 6 well culture plate. When 96-98% confluency was achieved, the insert frames were removed using sterile forceps to reach cell free gap. To create a reference point for subsequent measurements, three different part of the gap was marked on the underside of the plastic. Floating cells and cell debris were washed using PBS, relative culture medium was added to each wells and migration distance was photographed using a Zeiss Axiovert 24 light microscope at zero time in the marked areas. Afterward, the wells were treated by addition of DMSO as control and different increasing concentration of Pim and L741. Plates were then placed into the incubator and the cells were allowed to migrate until the time when the gap for the positive control closed (t time). Images were taken from the marked areas again. This assay was performed employing various concentrations of drugs at which maximum 5% viability inhibition was observed after 10 h treatment.

Transwell Migration Assay

This assay for confirmation of cell migration was performed using 96-well Costar Transwell chambers with 8.0 μm pore polycarbonate membranes (Corning Inc., Corning, N.Y.). Cell culture inserts transwells were placed in wells of 96 well plate. The bottom chambers were filled with 120 μl of cell culture medium containing 10% FBS. Cells suspended in 70 μl serum free medium with DMSO as negative control or drugs were added to the upper part of each chamber followed by incubation at 37° C. with 5% CO2. After 4 h the medium was aspirated from the top of chambers and the bottom side of chambers washed with PBS. Those that have penetrated to the bottom side of the membrane were detached with 0.25% trypsin/EDTA during 3 min (37° C.) followed by inactivation of trypsin with soybean (Sigma Aldrich). To compare the number of invaded cells in treatment conditions to the control untreated cells the CellTiterGlo® Luminescent cell viability assay were conducted. Six replicates were performed for each treatment condition to predict the responder outcome variable and the luminescence signal which is corresponding to the number of live suspended cells was measured. Graph was plotted according to the readings obtained. This assay was performed employing various concentrations of drugs at which maximum 5% viability inhibition was observed after 4 h treatment.

Example 1: Specific Detection of DRD2 in Chronic Pancreatitis and Pancreatic Cancer and not in Healthy Tissue FIG. 1 shows that DRD2 was detected in immersion fixed paraffin-embedded sections of pancreatic ductal cancer tissue 1(C) and chronic pancreatitis (B) but not in normal ductal cells 1(A) using a human monoclonal antibody. Tissues were then counterstained with hematoxylin.

Example 2: Immunohistochemical Analysis of DRD2 Levels Using a Large Number of Clinical Tissues, Tissue Microarray (TMA)

Distribution of DRD2 expression in clinical tissues revealed its high expression in PDAC and CP in comparison with mild positivity in pancreatic ducts normal samples (FIG. 2).

Example 3: Antagonists of DRD2 are Cytotoxic to Pancreatic Cancer Cells

Potent toxicity effect of pimozide, an FDA-approved drug and DRD2 antagonist, on the viability of pancreatic cancer cell lines (see FIG. 3A). The effect was specific to cancer cells but not as much to fibroblast (non-cancer cells).

The effect of pimozide was reproduced with another more selective DRD2 antagonist. Specific toxicity effect of L741, 626, a selective DRD2 antagonist, on the viability of pancreatic cancer cell lines is shown in FIG. 3B, and supports the finding that antagonists of dopamine receptors, in particular DRD2, are beneficial for a cancer treatment.

In order to assess whether the effect observed with pimozide and L-741,626 is indeed due to the action of DRD2, an RNAi experiment was conducted. Using shRNA targeting DRD2 expression is shown in FIG. 4. Also the RNAi construct significantly impaired tumor cell growth and viability compared to a control treatment.

All lentiviral shRNA vectors were retrieved from the arrayed Mission® TRC genome-wide shRNA collections purchased from Sigma-Aldrich Corporation. Additional information about the shRNA vectors can be found at http://www.sigmaaldrich.com/life-science/functional-genomics-and-rnai/shrna/library-information.html or http://www.broad.mit.edu/genome_bio/trc/rnai.html, using the TRCN number. The following lentiviral shRNA vectors targeting DRD2 were used: TRCN0000011342 and TRCN0000011343. Lentiviral supernatants were generated as described at http://www.broadinstitute.org/rnai/public/resources/protocols.

Example 4: Combination Treatment of DRD2 Antagonists Pimozide with Gemcitabine

Interestingly the use of increasing concentrations of pimozide in combination with a variety amount of gemcitabine in PANC-1 cells (FIG. 5).

Example 5: Inhibition of DRD2 Reduces Migration Capacity of Tumor Cells

PANC-1 tumor cell migration was tested in a scratching assay using pimozide and L-741,626 in increasing concentrations. Results are depicted in FIG. 6. The results indicate that tumor cell migration is affected by both pimozide and L-741,626 in a concentration dependent manner.

The impact on migration capacity of DRD2 antagonists was reproduced using PANC-1 and a different cell line (MiaPaca-2) in a Boyden Chamber Assay. Results are depicted in FIG. 7. Pimozide significantly reduced migrated cells both in the PANC-1 and MiaPac-2 cell line, in a concentration dependent manner.

Hence, the inhibition of DRD2 in pancreatic tumor cells not only reduces tumor cell viability and survival, but also reduces migrating cells which is beneficial to avoid the development of pancreatic metastasis.

Example 6: In-Vivo Inhibition of Tumor Growth

In order to monitor tumor growth in an in-vivo situation mice were implanted with PANC-1 cells expressing the negative control (pLKO) or shDRD2 (three mice per group, each implanted with cells in both flanks). There was a significant decrease in tumor growth in mice implanted with DRD2-deficient cells (p=0.002) as can be seen in FIG. 8A. Staining for Ki67, a marker of cell proliferation, confirmed decreased proliferation in DRD2-deficient cells. Analysis with an antibody against DRD2 confirmed the efficacy of knockdown (FIG. 8B).

Therefore, DRD2 inhibition significantly reduced pancreatic tumor growth in vivo.

The invention claimed is:

1. A method for treating pancreatic ductal adenocarcinoma or chronic pancreatitis in a subject in need thereof, said method comprising administering an antagonist of a dopamine receptor to the subject, wherein the antagonist of the dopamine receptor is selected from the group consisting of pimozide and L-741,626.

2. The method of claim 1, wherein said antagonist is pimozide.

3. The method of claim 2, wherein pimozide is administered in dosages of between about 0.01 to 5 mg/kg body weight/day.

4. The method of claim 3, wherein pimozide is administered in A dosages of about 0.2 mg/kg body weight/day.

5. The method of claim 3, wherein pimozide is administered orally.

6. The method of claim 1, wherein said antagonist is administered in combination with gemcitabine.

7. A combination for treatment of pancreatic ductal adenocarcinoma or chronic pancreatitis, comprising an antagonist of a dopamine receptor, together with at least one additional anti-cancer drug, wherein the antagonist of a dopamine receptor is selected from the group consisting of pimozide and L-741,626 and the additional anticancer drug is gemcitabine.

8. The combination of claim 7, wherein the antagonist is pimozide.

9. The combination of claim 8, wherein pimozide is provided in dosages of between about 0.01 to 5 mg/kg body weight/day.

10. A diagnostic method for detecting chronic pancreatitis or pancreatic ductal adenocarcinoma cells in a subject, comprising
   providing a biological sample derived from the pancreas of said subject,
   detecting the presence or absence of dopamine receptor D2 (DRD2) in said biological sample,
wherein the presence of DRD2 in said biological sample is indicative for the presence of pancreatic tumor cells or chronic pancreatitis.

11. The method of claim 10, wherein said biological sample is a pancreatic tissue sample.

12. The method of claim 10, wherein said sample is an immersion fixed paraffin embedded tissue sample.

13. The method of claim 10, wherein in step b. DRD2 is detected directly or indirectly by detecting DRD2 Mrna expression.

* * * * *